United States Patent [19]

Ambers et al.

[11] 4,338,280
[45] Jul. 6, 1982

[54] FLUID SAMPLING

[75] Inventors: Paul J. Ambers, Westwood; R. Barry Stevens, Chelmsford, both of Mass.

[73] Assignee: Instrumentation Laboratory Inc., Lexington, Mass.

[21] Appl. No.: 250,438

[22] Filed: Apr. 2, 1981

[51] Int. Cl.³ .......................... G01N 1/14; G01N 1/18
[52] U.S. Cl. .................... 422/68; 73/864.22; 422/81
[58] Field of Search ............. 422/68, 81, 100; 134/21; 73/864.22, 864.25

[56] References Cited

U.S. PATENT DOCUMENTS

| | | | |
|---|---|---|---|
| 3,842,680 | 10/1974 | Vollick | 73/425.4 P |
| 3,858,450 | 1/1975 | Jones | 73/423 A |
| 3,881,872 | 5/1975 | Naono | 422/81 X |
| 3,912,456 | 10/1975 | Young | 23/253 R |
| 3,949,615 | 4/1976 | Stein | 73/423 A |
| 3,963,440 | 6/1976 | Stein | 23/253 R |
| 4,000,973 | 1/1977 | Petersen | 23/230 R |
| 4,046,511 | 9/1977 | Stabile | 23/259 |
| 4,054,415 | 10/1977 | Seligson | 23/253 R |
| 4,076,503 | 2/1978 | Atwood | 23/259 |
| 4,131,426 | 12/1978 | Range | 141/1 |
| 4,210,724 | 7/1980 | Sogi | 435/292 |
| 4,217,780 | 8/1980 | O'Connell | 73/421 R |

Primary Examiner—Ronald E. Serwin

[57] ABSTRACT

A liquid sample analyzer has an analysis chamber adapted to receive sample material to be analyzed, sensor means coupled to the analysis chamber for providing an output signal related to a constituent of the sample material, and sampler apparatus that includes structure defining a sample intake flow path that has an inlet port and is connected to the analysis chamber, and rinse apparatus in communication with a waste system. A wiper member slides along the intake tube for wiping sample residue from the outer surface of the intake tube. A drive moves the sample inlet port between a sample intake position in which the inlet port is exposed to the operator and a reset position in which the inlet port is aligned with and the wiper is seated on the rinse apparatus. When the sample inlet port is in the sample intake position sample material is flowed into the sample intake flow path and when the sample inlet port is in reset position cleaning fluid is flowed through the sample flow path and against a surface of the wiper member for removing sample residue from the wiper member.

21 Claims, 10 Drawing Figures

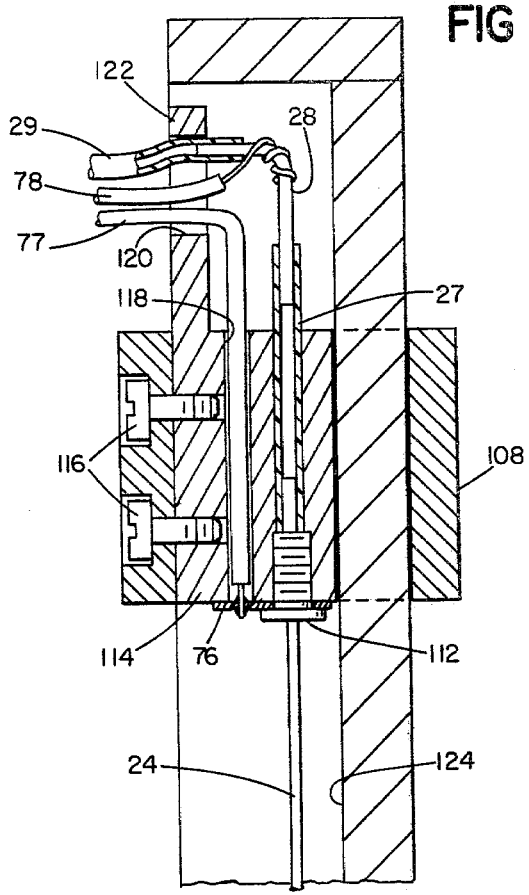
FIG 3
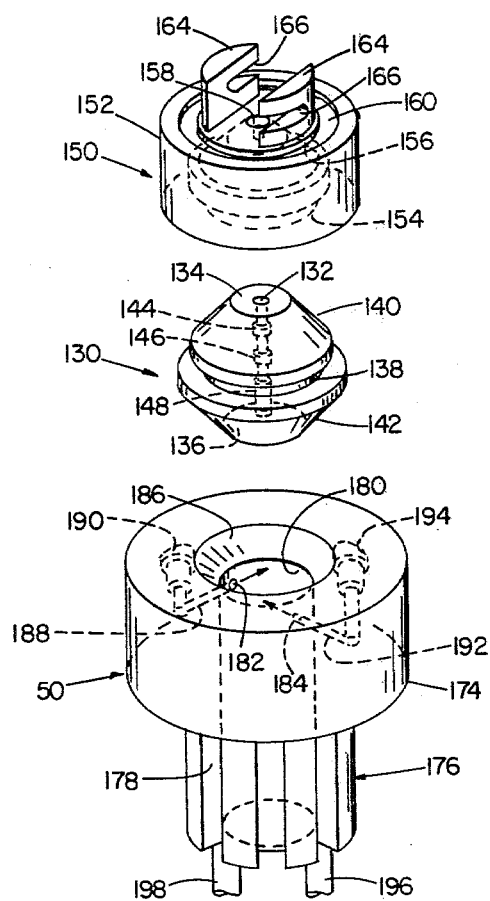
FIG 4
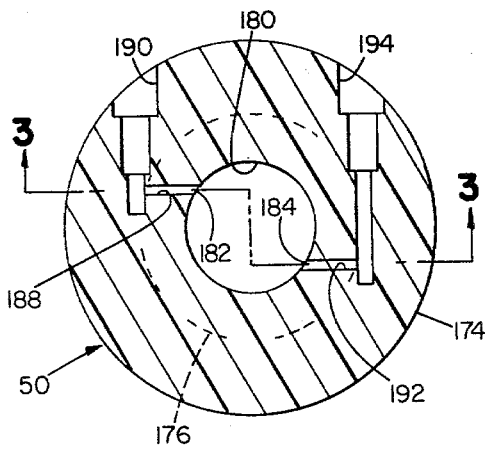
FIG 5
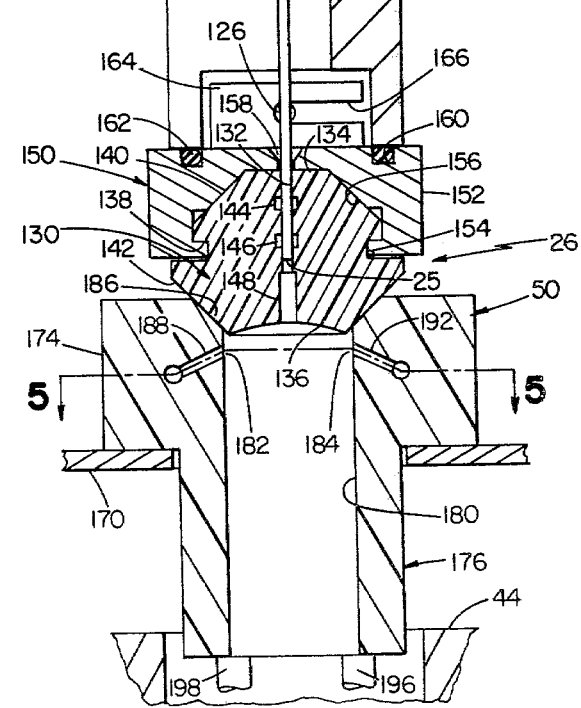

FLUID SAMPLING

This invention relates to fluid sampling and more particularly to automated sampler mechanisms of the self-cleaning type that are useful in clinical analysis systems.

Need exists in many fields for efficient and reliable sampler mechanisms capable of rapidly obtaining successive fluid samples to be analyzed without cross-contamination or intermixing between successive samples. One such field is clinical analysis where economics and cost effectiveness encourage nearly continuous operation with blood samples from different patients being analyzed in rapid succession. A problem of cross contamination between successive specimens exists, as in the case where a probe tube, a pipette, a dip tube or the like is used to aspirate or withdraw a specimen from the container, and it is necessary to avoid retention of a residue of sample on the outside of the tube since such retained sample material can represent a significant fraction of the sample. Conventionally, where specimens are individually pipetted, the transfer tube is wiped by the operator with tissue, which presents risks of incomplete wipe off and other problems such as possible infection of the operator in the case of particular fluids that may be analyzed. Also, intermixing or cross-contamination between successive samples could result in inaccurate data and incorrect diagnosis. Preferably, the sampler mechanism is adapted for operation by a relatively unskilled person who need only to deliver the sample to an entry port and actuate a starting switch. Simple, automatic, and rapid rinsing of the sampler mechanism between samples is desirable.

In accordance with one aspect of the invention there is provided a liquid sample analyzer of the type having an analysis chamber adapted to receive sample material to be analyzed, sensor means coupled to the analysis chamber for providing an output signal related to a constituent of the sample material, and sampler apparatus that includes structure defining a sample intake flow path that has an inlet port and is connected to the analysis chamber, and rinse apparatus for communication with a waste system. Associated with the sampler apparatus are drive means for moving the sample inlet port between a sample intake position and a reset position in which the inlet port is aligned with the rinse apparatus, first control means operative when the sample inlet port is in the sample intake position for flowing sample material through the inlet port into the sample intake flow path, sensor means responsive to flow of a predetermined quantity of sample material into the sample flow path for terminating intake of sample material and moving the inlet port to the reset position, and second control means operative when the sample inlet port is in reset position for flowing cleaning fluid through the sampler apparatus.

In accordance with another aspect of the invention, there is provided liquid sampling apparatus that includes a hollow sample intake tube having an inlet port adapted to be inserted into a sample container for transfer of sample material to be analyzed from the container, the intake tube being movable between a sample intake position and a reset position, means operable upon movement of the intake tube to said sample intake position for withdrawing fluid from the sample container through the intake tube, a wiper member slidable along the intake tube for wiping sample residue from the outer surface of the intake tube, and drive means for sliding the wiper member between a first position in which the inlet port is housed in the wiper member and a second position in which the inlet port extends forward of the wiper member.

In preferred embodiments, the rinse apparatus is arranged to receive the wiper member in reset condition, and the rinse apparatus includes means for directing a flow of cleaning liquid against a surface of the wiper member for removing sample residue from the wiper member. In a particular embodiment the intake tube is of stainless steel and has an inner diameter of less than one millimeter; the wiper member is a grommet-like element of about 50 Shore A durometer resilient material that has a through passage in which the intake tube is disposed with a lubricating liquid reservoir in communication with the through passage, a concave end surface and an annular seat surface surrounding the concave end surface; and the rinse apparatus includes a cooperating seat area for receiving the annular seat surface of the wiper member in sealing engagement. The wiper member includes a socket portion adapted to receive a capillary tube, and the system further includes means for moving the wiper member relative to the inlet port of the tube to detach a coupled sample source from the inlet port prior to return of the sampler inlet port to reset position. In that particular embodiment, the sampler includes a first drive motor for rotating the tube-wiper assembly between first and second angular positions, and a second drive motor for reciprocating the wiper along the tube, the drive shaft of the second drive motor being located on the axis of rotation of the tube-wiper assembly. A plurality of electrical conductivity sensor elements spaced along the intake path sense the intake of a microsample of sample material to be analyzed; and pump means (which may be separate or combined units) connected to the analysis chamber is driven in a first mode for drawing sample into the system and in a second mode for flowing cleaning liquid through the analysis chamber and the intake path in a backflushing action. The system also includes a valve arrangement connected between the analysis chamber and the pump means for venting the analysis chamber in a first condition and connecting the analysis chamber to one or more fluid sources in a second condition.

The system, in response to a first input command, presents the intake port to the operator for coupling to a sample container, and in response to a second input command draws a microsample from the container into the system. As soon as intake of the microsample is complete, the system automatically houses the intake port and returns the sampler mechanism to reset condition in communication with a waste container. With the sampler mechanism in reset condition, (the intake port housed and the wiper sealed against a rinse adaptor) the sample is analyzed and then the sampler is flushed and cleaned automatically with cleaning liquid being concurrently backflushed through the analysis chamber and the intake tube and jetted against wiper surfaces. The invention provides improved sampler mechanisms that are easy to operate, provide convenient intake of microsamples for analysis, and minimize cross-contamination between successive sample.

BRIEF DESCRIPTION OF THE DRAWINGS

Other features and advantages of the invention will be seen as the following description of a particular embodiment progresses, in conjunction with the drawings, in which:

FIG. 3 is a sectional view taken along the line 3—3 of FIG. 2;

FIG. 4 is an exploded view of components of the wiper and rinse adaptor assembly;

FIG. 5 is a sectional view taken along the line 5—5 of FIG. 3;

DESCRIPTION OF PARTICULAR EMBODIMENT

Figure 1:
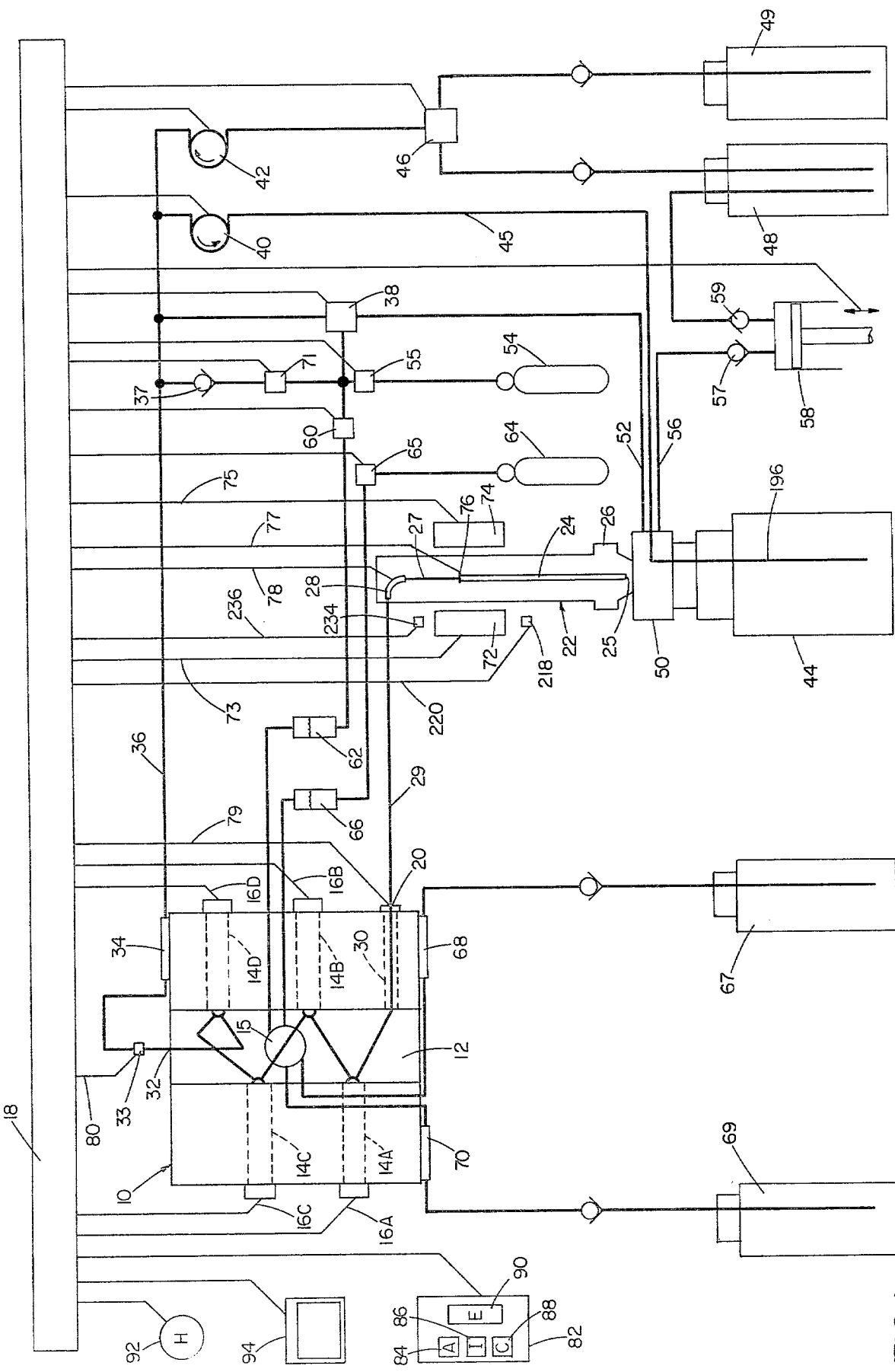
FIG. 1 is a diagrammatic view of a blood gas analysis system in accordance with the invention.

FIG. 1 is a diagrammatic view of a blood gas analysis system in accordance with the invention that includes an analysis chamber module 10 which includes analysis chamber structure 12 and associated sensors 14 that provide outputs over lines 16 to controller 18. Further details of module 10 may be had with reference to copending application Ser. No. 146,705 filed May 5, 1980, entitled ANALYSIS SYTEM, which application is assigned to the same assignee as this application and is expressly incorporated herein by reference. Connected to inlet 20 of analysis module 10 is sampler module 22 that includes intake tube 24 whose inlet port 25 is housed in wiper assembly 26 in reset position. Inlet tube 24 is connected through electrical insulator tube 27, electrically conductive elbow 28 and a second electrical insulator tube 29 to preheater 30 at inlet port 20 of analysis module 10. Outlet port 32 of module 10 is connected through sensors 33 and preheater 34 via line 36 to a check valve 37, three-way valve 38, the inlet of pump 40 and the outlet of pump 42. The outlet of pump 40 is connected to waste container 44 via line 45; and the inlet of pump 42 is connected via selector valve 46 to a flush solution reservoir 48 and to cleaning agent reservoir 49. Rinse adaptor 50, on which wiper assembly 26 is seated in reset position, has a line 52 for which gas is supplied from reservoir 54 when valves 55 and 38 are open; and a line 56 through which rinse liquid is supplied via injector pump 58 and check valves 57, 59 from reservoir 48. A first calibrating gas is supplied from container 54 through valves 55 and 60 and bubble chamber 62 to microvalve 15, a second calibrating gas from container 64 is supplied through valve 65 and bubble chamber 66 to microvalve 15; a first buffer is suppled from reservoir 67 through preheater 68 to microvalve 15; and a second buffer is supplied from reservoir 69 through preheater 70 to microvalve 15. In addition calibrating gas from container 54 is supplied through valve 71 to line 36.

Sampler assembly 22 includes rotation drive motor 72 which is controlled by signals over lines 73 from controller 18 and wiper drive motor 74 which is controlled by signals over lines 75 from controller 18. Sample sensing circuitry includes a first sensor 76 connected to probe tube 24 and to controller by line 77, a second connection from elbow 28 over line 78; a third connection from preheater 30 over line 79 (at inlet 20 of the analysis module 10); and a fourth connection from sensor 33 over line 80. The system also has keyboard 82 that includes, inter alia, three mode select keys: "Aspirate" key 84, "Inject" key 86, and "Capillary" key 88; and an "Enter" key 90; an operator alerting device 92; and a data display device 94 that are connected to controller 18.

Figure 2:
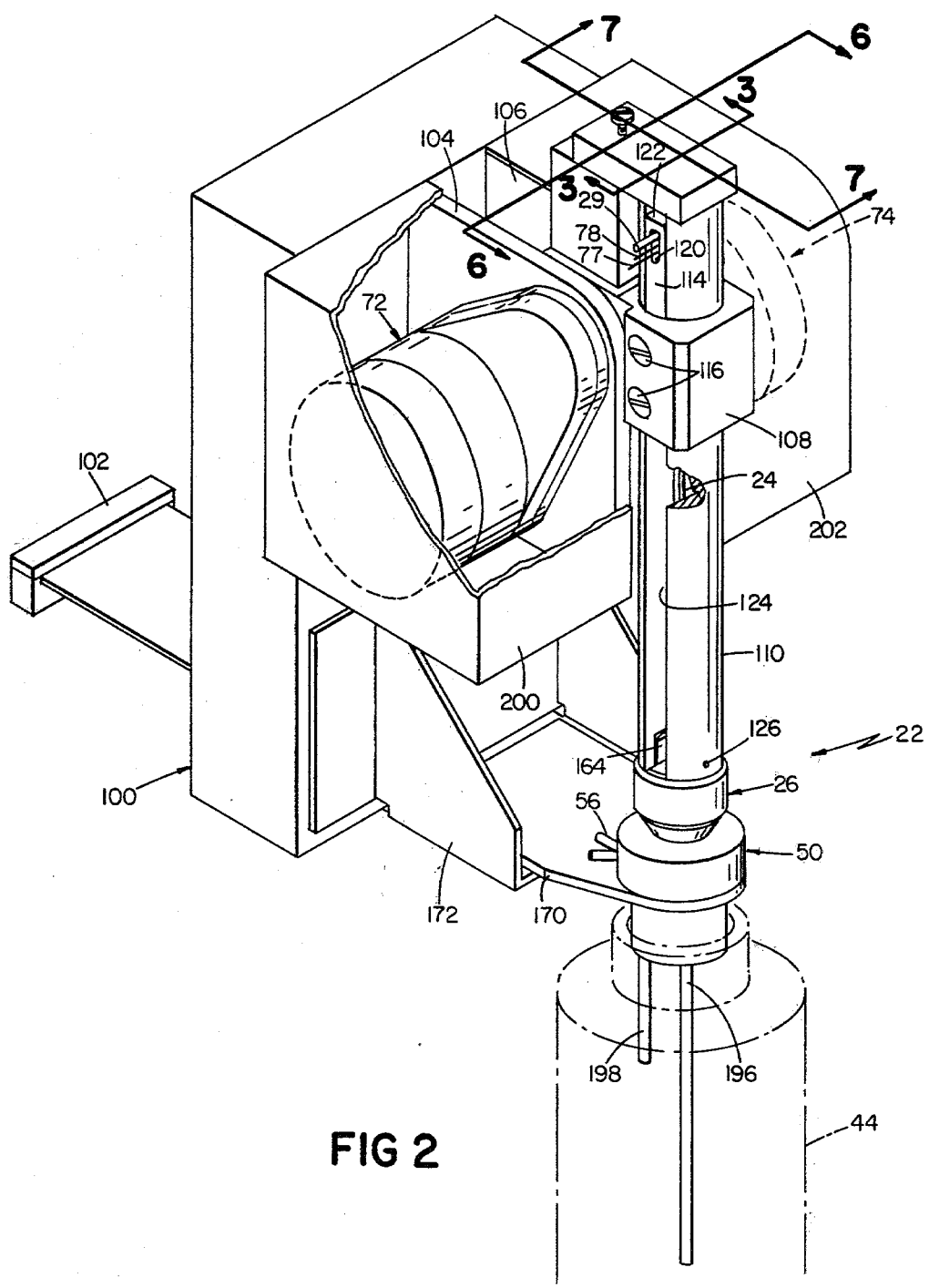
FIG. 2 is a perspective view of sampler apparatus employed in the system shown in FIG. 1.

Further details of sampler module 22 may be had with reference to FIGS. 2 and 3. That module includes support compartment 100 that houses electrical circuitry and has a rearwardly extending connector 102. Secured to and extending forwardly from compartment 100 are two parallel support plates 104, 106, between which is disposed an intake tube-wiper assembly that includes a support block 108 to which intake tube 24 (FIG. 3) is fixedly secured and a slider member 110 that is guided for reciprocation by block 108 and to which wiper assembly 26 is secured at its lower end.

Stainless steel inlet tube 24 has a length of about ten centimeters, an outlet diameter of about one millimeter and an inner diameter of about 0.8 millimeter. Soldered to inlet tube 24 is bushing 112 which is threaded into support block 114 that in turn is secured to guide block 108 by screws 116. Sensor lug 76 is seated against tube support block 114 by a flange of bushing 112 and a sensor wire 77 is soldered to lug 76 and passes through openings 118, 120 in support block 114. Connected to the upper end of inlet tube 24 is a nylon tube 27 that has an internal diameter of about one millimeter and a length of about 2.2 centimeters. Sensor wire 78 is soldered to stainless steel elbow 28 and extends through opening 120 in extension 122. A second nylon tube 29 that has an internal diameter of about one millimeter extends from elbow 28 to a stainless steel preheater tube 30 in analysis module 10; and a third sensor wire 79 (FIG. 1) is connected to that preheater tube.

Wiper assembly 26 is supported for longitudinal wiping movement along intake tube 24 by slider 110, a cylindrical member about 1.8 centimeters in diameter and about 12 centimeters in length that has an axially extending slot 124 in which intake tube 24 is disposed. Secured at the lower end of slider cylinder 110 are two opposed roll pins 126 that extend into slot 124 for securing wiper assembly 26 to slider cylinder 110. That wiper assembly, as shown in the exploded view of FIG. 4, includes a wiper grommet 130 molded of silicone rubber (G.E. Type SE4404U of about 50 Shore A durometer). Wiper grommet 130 has a diameter of about 1.6 centimeters and a height of about 1.4 centimeters, and has a through passage 132 (about one millimeter in diameter) that extends from planar upper surface 134 to concave lower surface 136 (of about 1.2 centimeters spherical radius). Wiper 130 also has an annular coupling groove 138, a conical upper surface 140 and a conical lower surface 142. Formed in passage 132 are two spaced lubrication chambers 144, 146 and a cylindrical socket portion 148 that has a diameter of about 1.3 millimeters and a length of about five millimeters.

Wiper coupling 150 has a cylindrical body portion 152 with a coupling flange 154 which receives annular groove 138 of wiper body 130 and an internal conical surface 156 against which wiper surface 140 seats; a through passage 158 for intake tube 24; an annular channel 160 that receives an O-ring 162; and two upstanding coupling arms 164, each of which has a horizontal slot 166. Wiper body 130 is resiliently secured to coupling 150 by mating engagement of flange 154 and annular groove 138 so that its upper conical surface 140 is seated against mating conical surface 156 of coupling 150. The wiper assembly 26 is inserted into the lower end of slider cylinder 110 so that pins 126 are aligned with slots 166. A 90 degree rotation of wiper assembly 26 seats pins 126 in the bottoms of slots 166 such that O-ring 162 is compressed and wiper assembly 26 firmly secured to slider cylinder 110.

Rinse adaptor 50 is supported on adjustable plate 170, as shown in FIG. 2, and plate 170 is seated on bracket 172 that projects forward from compartment 100, the position of support plate 170 being adjustable so that rinse adaptor 50 is aligned with intake tube 24 when in the position shown in FIG. 2. Further details of rinse adaptor 50 may be seen with reference to FIGS. 3-5. Adaptor 50 has a cylindrical body portion 174 about three centimeters in diameter and one centimeter in height and a depending tubular extension 176 that is about two centimeters in diameter and two centimeters in length, and in which is formed an array of axially extending vent slots 178. Body portion 174 has a through passage 180 that is about one centimeter in diameter in which are formed rinse fluid discharge ports 182 and 184; and a conical seat surface 186. Jet discharge passage section 188 slants upwardly at an angle of about 25 degrees (as indicated in FIG. 3) such that its discharge port 182 is located about one millimeter below the intersection of conical seat 186 and cylindrical through passage 180 and has coupling 190 for connection to check valve 57 (FIG. 1). Port 184 of a similar inclined jet discharge passage section 192 is offset from port 182 by about 0.6 centimeter (FIG. 5) and its coupling portion 194 is connected to valve 38 (FIG. 1). Also carried by rinse adaptor 50 is discharge tube 196 that is connected to feedback line 45, and level sensing electrode 198 that is connected to controller 18.

With reference again to FIG. 2, rotation drive 72 for sampler assembly 24 is a permanent magnet synchronous gear motor that is mounted on support plate 104 within housing 200, and drive 74 for reciprocating wiper 26 is a similar gear motor mounted in support plate 106 within housing 202. Further details of those drives may be seen with reference to FIG. 6. Output shaft 204 of motor 72 is geared to be driven at four rpm; and output shaft 206 of motor 74 is in opposed axial alignment with shaft 204 and is geared to be driven at 30 rpm. Guide block 108 is supported between plates 104, 106 by bearing assemblies 208, 210 for rotation about a horizontal axis with guide block 108 being secured in driving relation to motor shaft 204 by set screw 212 so that the assembly of inlet tube 24, wiper 26, guide block 108 and slide cylinder 110 are supported for rotation as a unit about the axis of motor shafts 204, 206 and is driven in rotation by motor 72 at a four rpm rate between a vertical position and a horizontal position as indicated in FIG. 7. Guide block 108 has an extension 214 (FIG. 7) which carries an adjustable switch actuator 216 which actuates microswitch 218 when the sampler assembly is in vertical position to provide a signal over line 220 to controller 18.

Figure 6:
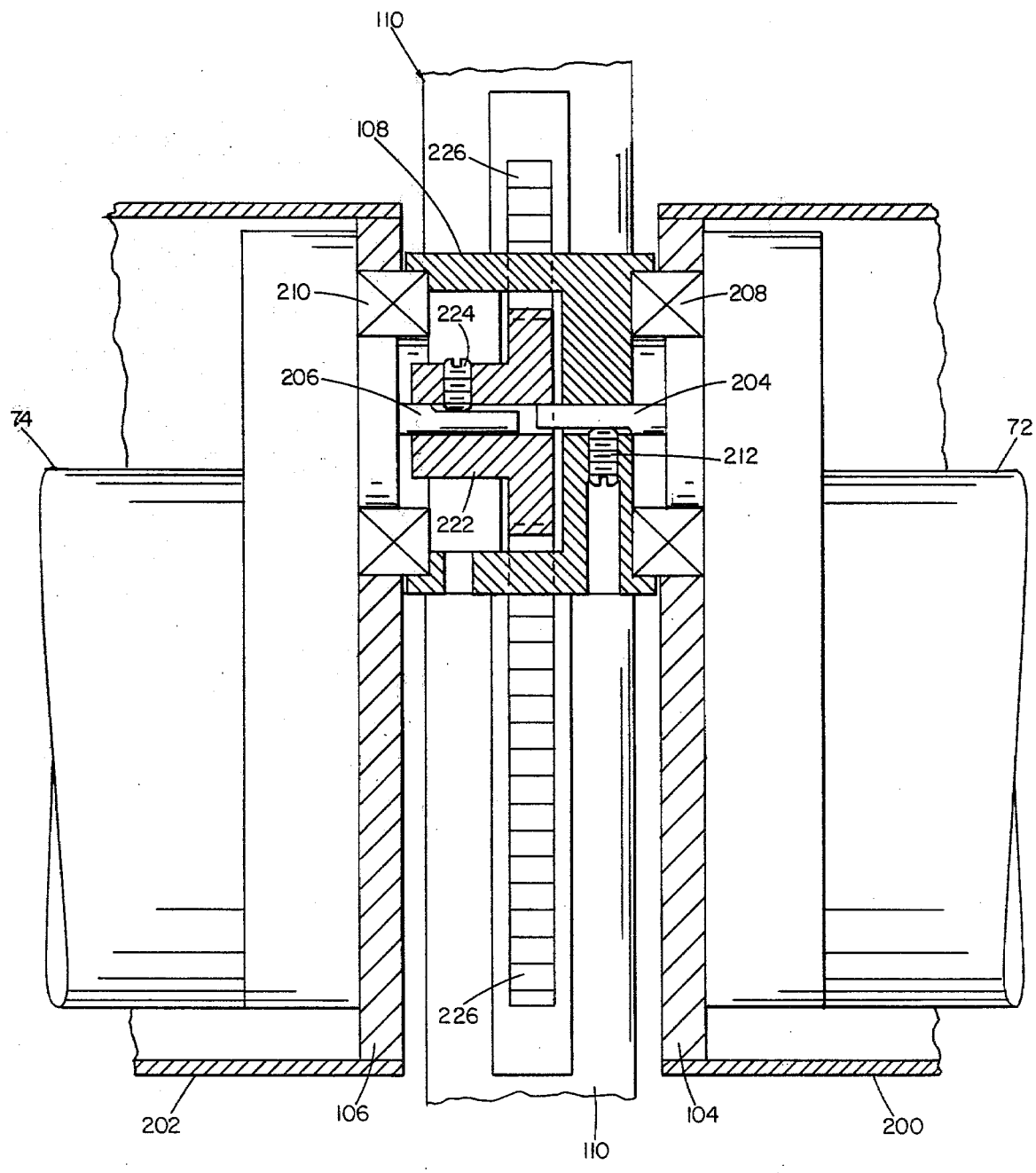
FIG. 6 is a sectional view taken along the line 6—6 of FIG. 2.
Figure 7:
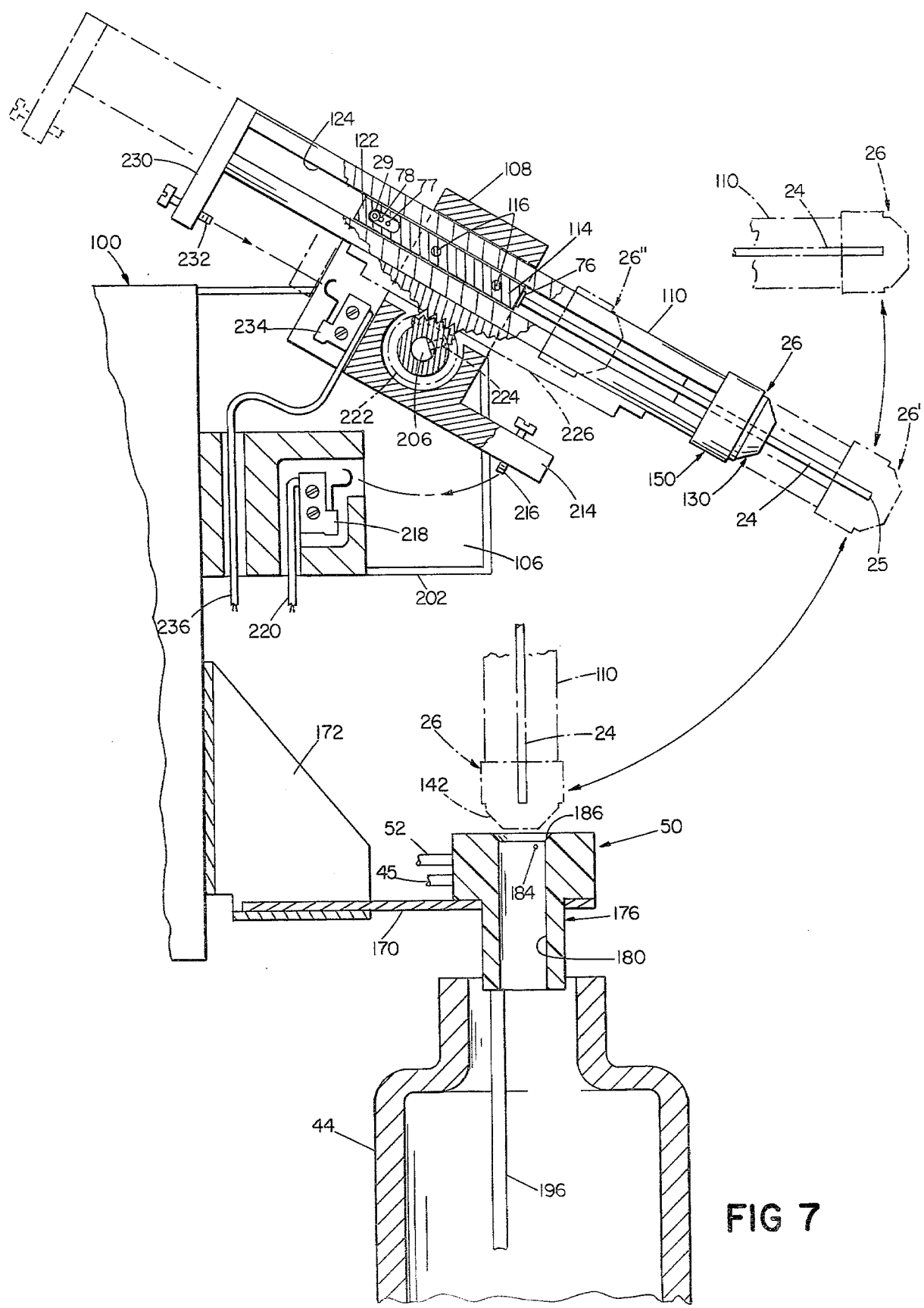
FIG. 7 is a sectional view taken generally along the line 7—7 of FIG. 2 showing operative positions of the sampler apparatus.

The drive assembly for reciprocating slider cylinder 110 includes motor 74 and spur gear 222 which is connected to output shaft 206 by set screw 224 (FIG. 6). Slider cylinder 110 extends through a cylindrical passage in guide block 108 and rack gear 226 is resiliently mounted on slider cylinder 110. Motor 74 reciprocates wiper 26 through spur gear 222 and rack gear 226 between an advanced position 26' (FIG. 7) in which the inlet port 25 of intake tube 24 is housed in wiper grommet 130 and a retracted position 26" in which about six centimeter length of inlet tube 24 projects beyond wiper 26. Arm 230, secured to the upper end of slide cylinder 110, carries an adjustable switch actuator 232 which engages microswitch 234 when wiper 26 is in its advanced position 26' to provide a signal over line 236 to controller 18.

When sampler assembly 22 is in its vertical position (as indicated by a signal from microswitch 218 over line 220) and wiper surface 142 is seated on conical seat 186 of rinse adaptor 50 (as indicated by a signal from microswitch 234 over line 236) inlet port 25 of intake tube 24 is housed in wiper 130 as indicated in FIG. 3. In this position, jets of rinse and drying fluids are discharged through ports 182, 184 against spherical surface 136 in swirling flow action to remove residue from surface 136 and recess 148. Concurrently rinse liquid is back flowed through intake tube 24 for discharge into waste bottle 44 to provide effective cleaning of wiper 130 and intake tube 24.

Figure 8:
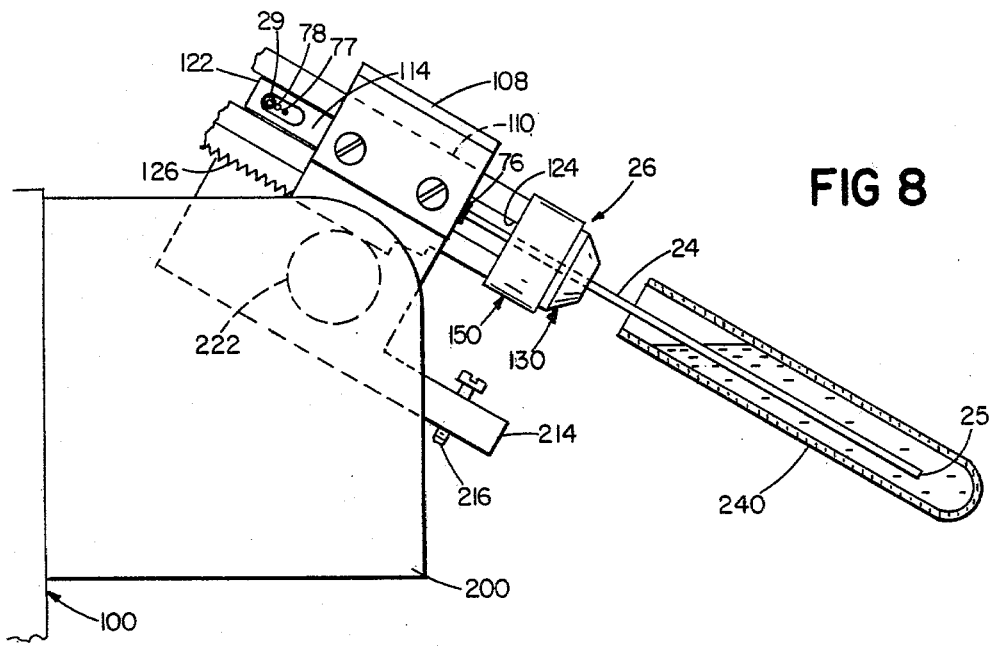
FIG. 8 is a diagram showing the sampler apparatus in an "aspirate" mode of operation.
Figure 9:
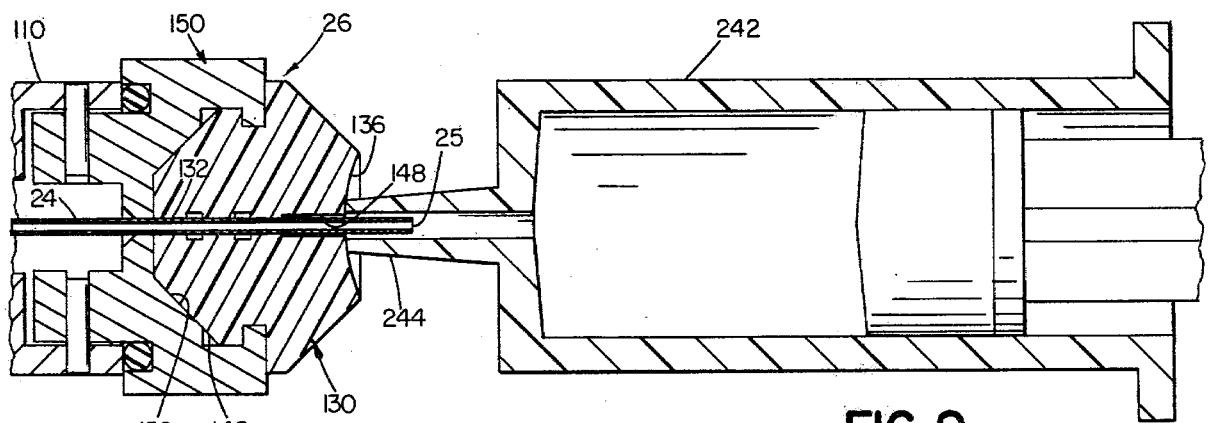
FIGS. 9 and 10 are diagrams showing the sampler apparatus in "inject" and "capillary" modes of operation respectively.

In system operation, in response to depression of Aspirate key 84, controller 18 energizes motor 72 to rotate sampler assembly 22 sixty degrees to the position shown in FIGS. 7 and 8 and energizes motor 74 to retract wiper assembly 26 to expose a six centimeter length of intake tube 24 (FIG. 8). The operator inserts inlet port 25 of intake tube 24 into sample container 240 as indicated in FIG. 8 and then depresses Enter key 90. In response to that signal, controller 18 energizes peristaltic pump 40 to rotate as indicated in FIG. 1, creating reduced pressure in intake tube 24 that draws sample from container 240 into the sample flow path. When the aspirated sample completes an electrical circuit between probe tube 24 and elbow 28, the resulting signals on lines 77 and 78 indicate that a 65 microliter volume sample has been aspirated from container 240 and pump 40 is deenergized. (In a second intake mode, sample intake continues until the sample has completed an electrical circuit between signal lines 77 and 79, indicating that a 120 microliter volume sample has been flowed into the system.) Controller 18 signals the intake of the predetermined volume of microsample by energization of horn 92 which alerts the operator to withdraw the sample container. Motor 74 then advances wiper assembly 26 (forcing container 240 from tube 24 if the container has not been removed by the operator), wiping residue of sample liquid from the outer surface of intake tube 24. When port 25 is housed in wiper 26 (as signalled by microswitch 234) motor 72 is energized to rotate the sampler assembly to vertical position (signalled by microswitch 218). In that vertical position motor 74 is again energized by controller 18 to drive wiping grommet 130 downward until limit switch 234 is again triggered so that grommet surface 142 is firmly seated on cooperating conical surface 186 of rinse adaptor 50 (FIG. 3).

In this sampler reset condition, controller 18 again energizes pump 40 to bring the inducted volume of sample past the gas electrodes 14A and 14B until the leading edge of sample touches microvalve 15. Electrical continuity is detected and pump 40 is stopped for fifteen seconds for equilibration of the gas electrodes. At this stoppage of pump 40, vent valve 38 opens briefly to relieve the negative pressure and prevent over travel of the sample.

After the fifteen second pause, pump 40 draws the sample column to sensor 33 at the near end of flush preheater 34. Pump 40 stops and valve 38 again vents line 36. Sample analysis is then performed with the results being displayed at display 94.

Controller 18 then energizes pump 42 and operates valves 46, 55 and 71 so that flush solution will be mixed with gas for more efficient cleaning. One second after valve 71 opens, flush pump 42 is started and flush solution and gas are driven back through the sample flow path in analysis module 10, the flush solution being equilibrated to the calibrating gas from container 54 and flowing through microvalve 15 and past electrodes 14A and 14B, through preheater 30 and sampler 22 into waste bottle 44. Pump 42 runs for fifteen seconds, with valve 71 being closed two seconds before pump 42 stops.

Following this back flush, pump 40 is first driven at a slow rate to flow the flush solution remaining in the sample path directly to waste bottle 44. After twenty seconds, pump 40 is driven at a faster rate for an additional five seconds to draw droplets out of the system.

While the forward flush goes on, injector pump 58 is operated twice, flowing two 200 microliter volume pulses of flush solution to adaptor 50 for discharge through jet passage 188 against the spherical end surface 136 of wiper grommet 130 in a swirling, wiper surface cleaning action to clean the sample tip and wiper. Controller 18 then energizes solenoid valves 55 and 38 to flow pressurized gas from container 54 through valves 55 and 38 and jet passage 192 to dry spherical wiper surface 136 and the lower portion of passage 132.

Thus the system, in response to depression of Aspirate key 84, presents inlet port 25 to the operator for insertion of a sample container 240, and in response to depression of Enter key 90 draws a microsample from container 240 into the system. As soon as intake of the microsample is complete, the system automatically houses the inlet port 25 and returns the sampler mechanism to reset condition in communication with waste container 44. With the sampler mechanism in reset condition, (inlet port 25 housed and wiper 26 sealed against rinse adaptor 50) the sample is analyzed and then the sampler is flushed and cleaned automatically with cleaning liquid being back flushed through the analysis chamber and the intake tube and concurrently jetted against wiper surfaces.

With other modes of sample introduction, the sample traverses the same path through the analysis module and is followed by the same flush cycle. For small (65 microliter) microsamples the sample is initially stopped at elbow 28, while a larger (120 microliter) sample is initially stopped at preheater 30. Microvalve 15 is driven by a stepper motor and can assume any of three positions—"Sample", "Cal 1", or "Cal 2". The sample and flush operations occur with the microvalve in the "Sample" position. The "Cal 1" position directs gas from container 54 to the gas electrodes and a 7.384 buffer from reservoir 67 to the pH electrode 14C; while the "Cal 2" position directs gas from container 64 to the gas electrodes 14A and 14B and 6.840 buffer from reservoir 69 to the pH electrode 14C, the buffer selected by microvalve 15 being drawn through the pH passages towards waste bottle 44 by pump 40.

A second mode (Inject) of operation is initiated when the operator depresses Inject key 86. The operator presents syringe 242 (or other injection device such as a Douglass (or similar gas bag). In this mode, a four millimeter length of sample tube 24 is exposed by wiper 26 so that the tip 25 penetrates the throat of the syringe 242. The operator then presents syringe 242, the pressing action of throat passage 244 against wiper surface 136 acting to enhance sealing of the wiper passage 132 against tube 24 due to interaction of conical surface 140 and 156. In response to depression of Enter key 90 by the operator, controller 18 opens vent valve 38 to (bypass pump) 40 and to connect the output of analysis module 10 via line 52 to rinse adaptor 50. The operator then injects sample into intake tube 24, injection of a predetermined microsample volume being indicated by audible indicator 92 in response to completion of a circuit between conductivity sensors 28 and 76 or between sensors 30 and 76. The operator then removes the injection syringe 242. Vent valve 38 is closed by controller 18; motor 74 is energized to advance wiper 26 to house inlet port 25 and wipe liquid from the outer surface of tube 24; and motor 72 rotates the sampler assembly 22 to reset position. When wiper 26 is seated on rinse adaptor 50 (as indicated by microswitches 218 and 234), controller 18 moves the microsample to the analysis module 10, an analysis is performed, the sample is back flushed and the wiper cleaned as previously described.

Figure 10:
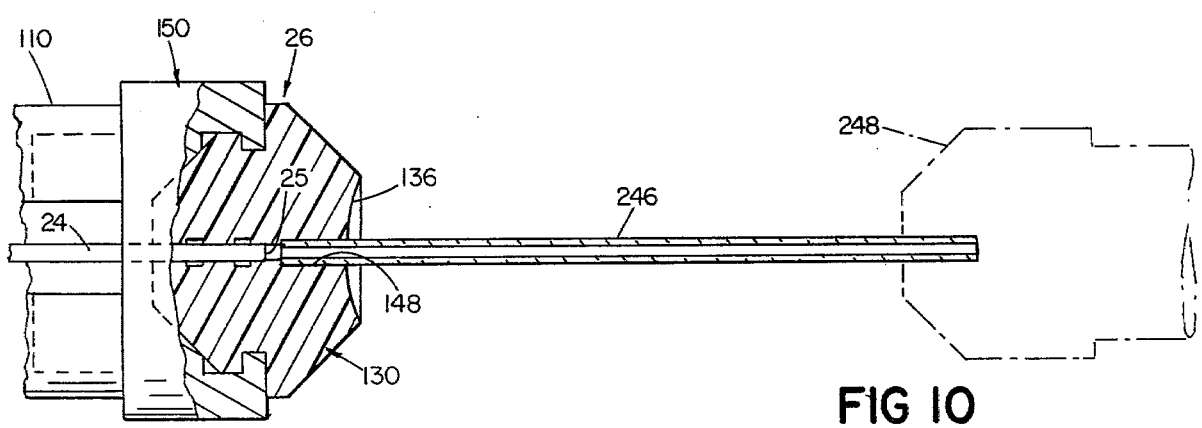

In a third mode of operation a sample is aspirated from a capillary tube 246 as indicated in FIG. 10. In response to depression of Capillary key 88 by the operator, controller 18 energizes motor 72 to rotate the sampler assembly to horizontal position with the inlet port 25 of intake tube 24 remaining housed in wiper assembly 26 as indicated in FIG. 10. In that position, the operator inserts capillary tube 246 into recess 148 and attaches a micropipette 248. Depression of Enter key 90 causes controller 18 to operate pump 40 to aspirate a microsample intake, of which is signalled by indicator 92. Wiper 26 is then first retracted a short distance to force tube 246 out of socket 148 (by tube 24) and then advanced to again house tube tip 25. The sampler mechanism 22 then returns to vertical (reset) position with wiper assembly 26 seated on the rinse adaptor 50. The sample is then drawn into the analysis chambers, analyses are performed, and the sampler is back flushed and the wiper cleaned as previously described.

While a particular embodiment of the invention has been shown and described, various modifications thereof will be apparent to those skilled in the art. It is therefore not intended that the invention be limited to the disclosed embodiment or to details thereof and departures may be made therefrom within the spirit and scope of the invention.

What is claimed is:

1. A liquid sample analyzer of the type having an analysis chamber adapted to receive sample material to be analyzed, sensor means coupled to said analysis chamber for providing an output signal related to a constituent of the sample material, sampler apparatus including structure defining a sample intake flow path that has an inlet port and is connected to said analysis chamber, rinse apparatus for communication with a waste system, said sample intake port and said rinse apparatus being movable relative to one another between a first position in which said inlet port is exposed to the operator and a second position in which said inlet port is aligned with said rinse apparatus, drive means for moving said sample inlet port and said rinse apparatus between said first and second positions, and a sampler control arrangement including means operative when said sample inlet port is in said first position for flowing sample material through said inlet port into said sample intake flow path defining structure, sensor means responsive to flow of a predetermined quantity of sample material into said sample flow path defining structure for terminating intake of sample material and energizing said drive means to move said inlet port and said rinse apparatus to said second position, and means operative when said sample inlet port is in said second position for flowing cleaning fluid through said sampler apparatus.

2. The system of claim 1 wherein said sample-intake flow path includes an intake tube that defines said inlet port and further including wiper structure arranged for movement relative to said intake for wiping sample residue from the outer surface of said intake tube, said wiper structure being seated on said rinse apparatus in said second position.

3. The system of claim 2 wherein said rinse apparatus includes means for directing a flow of cleaning fluid against a surfce of said wiper structure for removing sample residue from said wiper structure.

4. The system of claim2 or 3 wherein said intake tube is of relatively rigid material and has an inner diameter of less than one millimeter, and said wiper structure includes a member of resilient material that has a through passage in which said intake tube is disposed, said wiper member being arranged for sliding movement along said tube.

5. The system of claim 4 wherein said wiper structure further includes a lubricating liquid reservoir in communication with said through passage.

6. The system of claim 4 wherein said intake tube is of electrically conductive metal and said wiper structure member has a durometer of about 50 Shore A.

7. The system of either claim 4 or 6 wherein said wiper member has a concave end surface and an annular seat surface surrounding said end surface, and said rinse apparatus includes a cooperating seat area for receiving said annular seat surface of said wiper member in sealing engagement, and a jet port in said rinse apparatus for directing a jet of cleaning fluid against said concave end surface.

8. The system of claim 4 wherein said through passage in said wiper member includes a socket portion for receiving a capillary tube.

9. The system of either claim 2 or 8 and further including means for moving said wiper structure relative to said inlet port of said tube to detach a coupled sample source from said inlet port prior to return of said sampler inlet port to said second position.

10. The system of claim 2 wherein said drive means includes a first drive motor for rotating the tube-wiper assembly between first and second angular positions, and further including a second drive motor for reciprocating movement of said wiper along said tube, said second drive motor having a drive shaft located on the axis of rotation of said tube-wiper assembly.

11. The system of claim 1 wherein said sensor means includes a plurality of spaced electrical conductivity sensor elements spaced along said intake path for sensing the intake of a microsample of sample material to be analyzed.

12. The system of claim 1 wherein said control arrangement includes pump means connected to said analysis chamber, and means to drive said pump means in a first mode for drawing sample into said sampler and in a second mode for flowing cleaning liquid through said analysis chamber and said intake path in a back flushing action.

13. The system of claim 12 further including a valve arrangement connected between said analysis chamber and said pump means, said valve arrangement having a first condition connecting said analysis chamber to a source of calibrating gas for equilibrating said sensor means when said pump means is in said second mode and a second condition venting said analysis chamber when said pump means is in said first mode.

14. Automatic self-cleaning liquid sampling apparatus comprising a hollow sample intake tube having an inlet port adapted to be inserted into a sample container for transfer of sample material to be analyzed from the container, said intake tube being movable between a sample intake position and a reset position, means responsive to movement of said intake tube to said sample intake position for withdrawing fluid from the sample container through said intake tube, a wiper member slidable along said intake tube for wiping sample residue from the outer surface of said intake tube, and drive means for sliding said wiper member between a first position in which said inlet port is housed in said wiper member and a second position in which said inlet port extends forward of said wiper member.

15. The apparatus of claim 14 and further including rinse apparatus in communication with a waste system, said drive means seating said wiper member on said rinse apparatus in said reset position, and said rinse apparatus includes means for directing a flow of cleaning fluid against a surface of said wiper member for removing sample residue from said wiper member.

16. The system of claim 15 wherein said wiper member has a concave end surface and an annular seat surface surrounding said end surface, and said rinse apparatus includes a cooperating seat area for receiving said annular seat surface of said wiper member in sealing engagement, and a jet port in said rinse apparatus for directing a jet of cleaning fluid against said concave end surface.

17. The apparatus of claim 14 wherein said wiper member includes a socket for receiving a capillary tube, and interlock means for moving said wiper along said inlet intake tube to cause said intake tube to remove a capillary tube from said socket prior to movement of said sampler apparatus from said sample intake position to said reset position.

18. The apparatus of either claim 14 or 16 wherein said intake tube is of electrically conductive metal for connection in circuit as an electrical conductivity sensor element, and said wiper member is of resilient material of about 50 Shore A durometer and has a through passage in which said intake tube is disposed.

19. The apparatus of claim 15 and further including a first drive motor for rotating the tube-wiper assembly between first and second angular positions, and a second drive motor for reciprocating movement of said wiper member along said tube, said second drive motor having a drive shaft coaxial with the drive shaft of said first drive motor.

20. The apparatus of claim 19 and further including an analysis chamber connected to said sample intake tube for receiving sample material to be analyzed, sensor means coupled to said analysis chamber for providing an output signal related to a constituent of the sample material, pump means connected to said analysis chamber and operative in a first mode for drawing sample material through said intake tube into said analysis chamber and in a second mode for flowing cleaning liquid through said analysis chamber and said intake tube in a back flushing action, and a valve arrangement connected between said analysis chamber and said pump means, said valve arrangement having a first condition connecting said analysis chamber to a source of calibrating gas for equilibrating said sensor means when said pump means is in said second mode, and a first condition venting said analysis chamber when said pump means is in said first mode.

21. The apparatus of claim 20 wherein said intake tube has an inner diameter of less than one millimeter, said wiper member has a through passage in which said intake tube is disposed, a concave end surface, an annular seat surface surrounding said end surface, and a socket portion in said through passage for receiving a capillary tube; said rinse apparatus includes a cooperating seat area for receiving said annular seat surface of said wiper member in sealing engagement and a jet port for directing a jet of cleaning fluid against said concave end surface, and cleaning liquid flow means operative when said pump means is in said second mode and the annular seat surface of said wiper surface is seated on the cooperating seat area of said rinse apparatus for flowing cleaning liquid through said jet port against said concave end surface and into said socket portion of said wiper member.

* * * * *